(12) United States Patent
Serway

(10) Patent No.: US 10,711,238 B2
(45) Date of Patent: Jul. 14, 2020

(54) METHOD FOR PROLIFERATION OF CELLS WITHIN A BIOREACTOR USING A DISPOSABLE PUMPHEAD AND FILTER ASSEMBLY

(71) Applicant: Spectrum, Inc., Rancho Dominguez, CA (US)

(72) Inventor: David Serway, Rockville, MD (US)

(73) Assignee: Repligen Corporation, Waltham, MA (US)

(*) Notice: Subject to any disclaimer, the term of this patent is extended or adjusted under 35 U.S.C. 154(b) by 365 days.

(21) Appl. No.: 15/095,435

(22) Filed: Apr. 11, 2016

(65) Prior Publication Data

US 2016/0222337 A1 Aug. 4, 2016

Related U.S. Application Data

(63) Continuation-in-part of application No. 13/633,272, filed on Oct. 2, 2012, now abandoned.

(51) Int. Cl.
*C12M 1/00* (2006.01)
*C12N 1/02* (2006.01)
*C12Q 3/00* (2006.01)

(52) U.S. Cl.
CPC ............ *C12M 47/02* (2013.01); *C12M 29/10* (2013.01); *C12M 29/16* (2013.01); *C12M 29/18* (2013.01);
(Continued)

(58) Field of Classification Search
CPC ...... C12M 29/10; C12M 29/16; C12M 29/18; C12M 47/02; C12M 47/12; C12N 1/02; C12Q 3/00
(Continued)

(56) References Cited

U.S. PATENT DOCUMENTS 4,037,984 A 7/1977 Rafferty et al.
4,918,019 A * 4/1990 Guinn .................... C12M 29/12
435/286.5
(Continued)

FOREIGN PATENT DOCUMENTS

DE 10-2013-010724 A1 12/2014
EP 0673753 A1 9/1995
(Continued)

OTHER PUBLICATIONS

International Search Report and Written Opinion for PCT/US2017/026926 filed Apr. 11, 2017.
(Continued)

*Primary Examiner* — Liban M Hassan

(57) ABSTRACT

A method for promoting biological activity uses a filter system to increase cell production of a fed batch bioreactor. The filter system cycles bioreactor fluid through a hollow fiber tangential flow filter which separates metabolic wastes (as well as proteins) from cells produced in bioreactor and returned to fed batch bioreactor, improving cell production in the fed batch bioreactor. The filter system includes a disposable pump and filter, and a reusable control system. The pump is a low shear gamma stable pump gently cycling bioreactor fluid through the filter with minimal damage to the cells produced in the bioreactor. The pumphead and hollow fiber tangential flow filter are disposable. The pump motor is part of the control system and is reusable. The pumphead and filter are provided as an assembled and pre-sterilized unit allowing simple and quick attachment to the fed batch bioreactor, and simple and quick disposal.

7 Claims, 8 Drawing Sheets

(52) U.S. Cl.
CPC ............... *C12M 47/12* (2013.01); *C12N 1/02* (2013.01); *C12Q 3/00* (2013.01)

(58) Field of Classification Search
USPC .......................................... 435/289.1, 297.4
See application file for complete search history.

(56) References Cited

U.S. PATENT DOCUMENTS

| | | | |
|---|---|---|---|
| 5,885,456 | A | 3/1999 | Charkoudian et al. |
| 5,911,222 | A | 6/1999 | Lawrence et al. |
| 6,121,042 | A | 9/2000 | Peterson et al. |
| 6,632,658 | B1 | 10/2003 | Schoeb |
| 6,670,169 | B1 | 12/2003 | Schob et al. |
| 2004/0256329 | A1 | 12/2004 | Meserol et al. |
| 2005/0069426 | A1 | 3/2005 | Mason et al. |
| 2005/0112542 | A1* | 5/2005 | West ...................... C12M 41/48 435/3 |
| 2005/0158851 | A1† | 7/2005 | Furey |
| 2005/0260175 | A1† | 11/2005 | Hedrick |
| 2006/0118472 | A1 | 6/2006 | Schick et al. |
| 2006/0233777 | A1* | 10/2006 | Piva ...................... A61K 38/164 424/94.2 |
| 2007/0201993 | A1 | 8/2007 | Terentiev et al. |
| 2007/0235889 | A1 | 10/2007 | Hartounian et al. |
| 2010/0015204 | A1* | 1/2010 | Hedrick .................. A61F 2/442 424/423 |
| 2010/0041132 | A1 | 2/2010 | Hoerstrup et al. |
| 2010/0193434 | A1 | 8/2010 | Shinkazh |
| 2010/0230950 | A1* | 9/2010 | Williams ................ F16L 37/30 285/38 |
| 2011/0201100 | A1† | 8/2011 | Proulx |
| 2012/0250450 | A1† | 10/2012 | Ho |
| 2012/0294836 | A1* | 11/2012 | Rowley ................ B01D 61/145 424/93.7 |
| 2013/0115588 | A1* | 5/2013 | Davis ..................... C12M 23/28 435/3 |
| 2013/0200005 | A1* | 8/2013 | Mangiacotti ......... B01D 61/145 210/741 |

FOREIGN PATENT DOCUMENTS

| | | | | |
|---|---|---|---|---|
| EP | 0743085 A2 | 11/1996 | | |
| JP | 2013-150961 A | 8/2013 | | |
| WO | WO-2014051503 A1 * | 4/2014 | ............ | C12M 29/10 |

OTHER PUBLICATIONS

MilliporeSigma Process Solutions, "Interphex 2011 Product Demo: Mobius CellReady 200 L Bioreactor System", Apr. 14, 2011, YouTube, https://www.youtube.com/watch?v=1OD5-AqTZCw.†
U.S. Appl. No. 61/457,467, filed Apr. 1, 2011, published Oct. 4, 2012.†

\* cited by examiner
† cited by third party

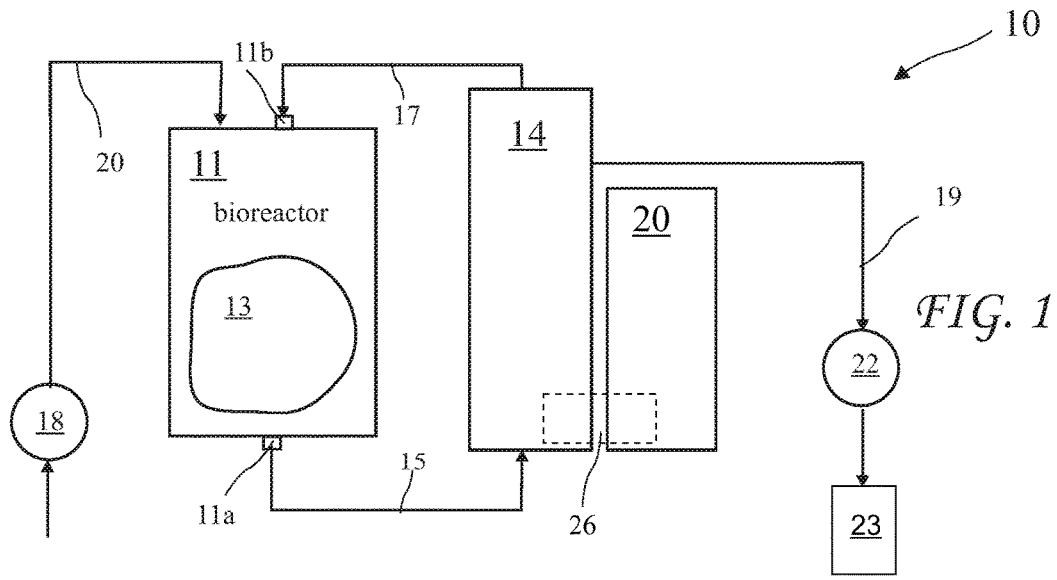
FIG. 1
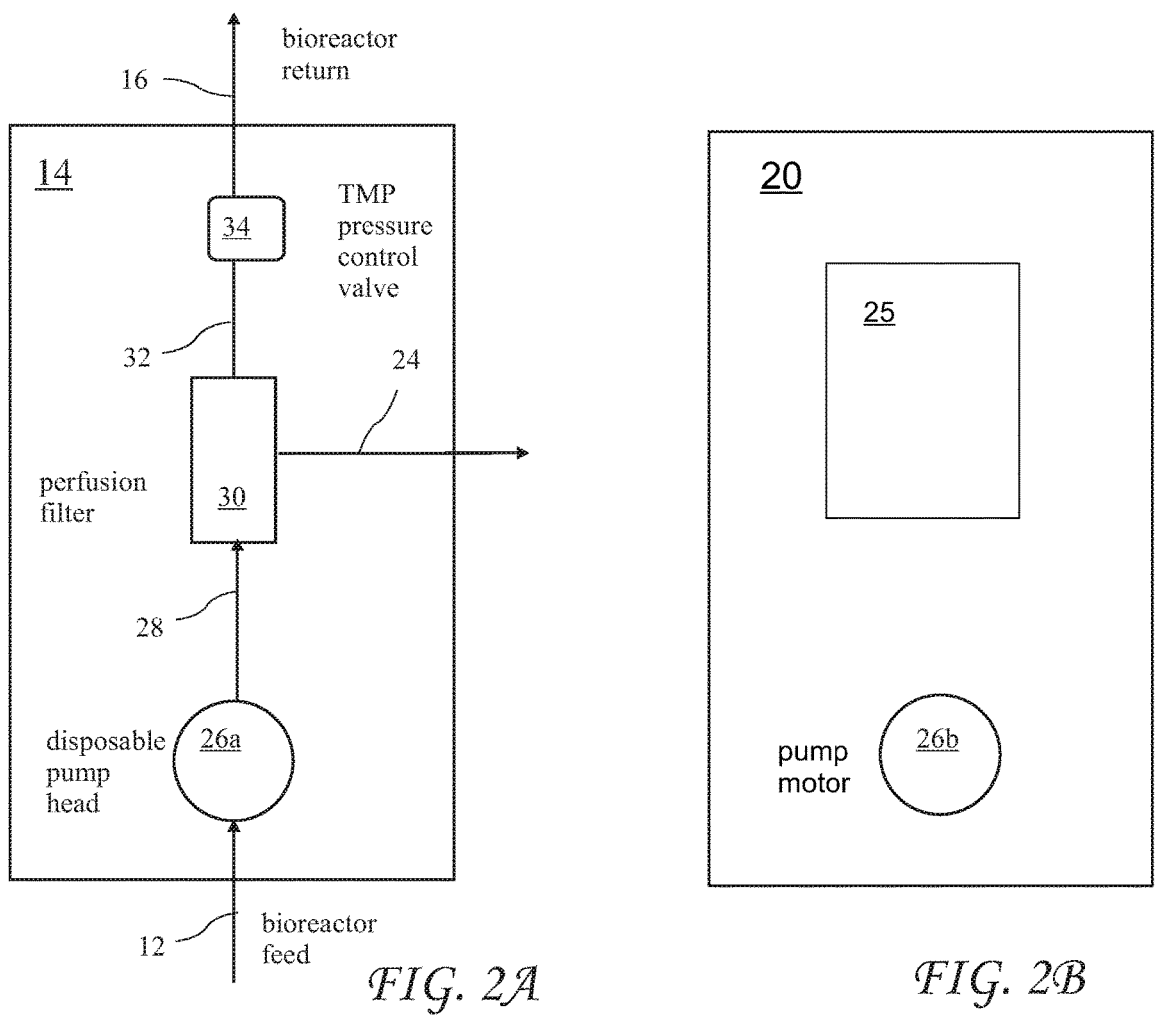
FIG. 2A
FIG. 2B

METHOD FOR PROLIFERATION OF CELLS WITHIN A BIOREACTOR USING A DISPOSABLE PUMPHEAD AND FILTER ASSEMBLY

CROSS-REFERENCE TO RELATED APPLICATIONS

The present application is a Continuation In Part of U.S. patent application Ser. No. 13/633,272 filed Oct. 2, 2012 which application is incorporated in its entirety herein by reference.

BACKGROUND OF THE INVENTION

The present invention relates to bioreactors and in particular to an improved bioreactor system and method including a disposable pumphead and tangential flow filter.

Bioreactor systems provide an environment supporting biological activity and known bioreactor systems build up metabolic waste in the bioreactor. The buildup of build up metabolic waste limits the amplification or cell growth within the bioreactor. As a result, known high capacity bioreactor systems require either a very large and expensive bioreactor or require filtering biological material in the bioreactor to continue the biological activity. Known pump and filter systems used for such filtering require a sterile environment. Components in the pump include parts which in some instances require replacement between each run. Mechanical pump components which wear or tear may give off debris into the bioreactor filter. Unfortunately, when pumps or filters of known systems require service or replacement, the required procedures can be time consuming due to the requirement to maintain the sterile environment.

BRIEF SUMMARY OF THE INVENTION

The present invention addresses the above and other needs by providing a method for promoting biological activity uses a filter system to increase cell production of a fed batch bioreactor. The filter system cycles Bioreactor fluid through a hollow fiber tangential flow filter which separates metabolic wastes (as well as proteins) from cells produced in Bioreactor and returned to fed batch bioreactor, improving cell production in the fed batch bioreactor. The filter system includes a disposable pump and filter, and a reusable control system. The pump is a low shear gamma stable pump gently cycling bioreactor fluid through the filter with minimal damage to the cells produced in the bioreactor. The pumphead and hollow fiber tangential flow filter are disposable. The pump motor is part of the control system and is reusable. The pumphead and filter are provided as an assembled and pre-sterilized unit allowing simple and quick attachment to the fed batch bioreactor, and simple and quick disposal.

In accordance with one aspect of the invention, there is provided a tangential flow filter system including a disposable, low shear pumphead. The disposable, low shear pumphead allows filtering bioreactor fluid without contamination or damage to cells. A preferred disposable pumphead includes no mechanical interaction between parts, and includes magnet elements which rotate in the presence of a rotating magnetic field, effectively as a rotor in an electric motor. An example of a preferred pump is made by Levitronix in Switzerland (Zurick) with offices in Waltham, Mass. The time to set-up, flush and sterilize known perfusion systems which do not include a disposable pumphead is extensive in comparison to the pumphead of the present invention. The disposable low shear recirculating pumphead, tangential flow filter, and associated tubing are pre-sterilized and aseptically connectable to the bioreactor.

In accordance with another aspect of the invention, there is provided a tangential flow filter system including either manual or automatic control of a perfusion process. Some modes of operation are designed for seed reactors, continuous perfusion reactors, concentrated fed batch perfusion as well as cell or cell debris clarification (post transfection or Cell Lysis).

In accordance with still another aspect of the invention, there is provided a disposable perfusion tangential flow filter system which decreases existing bioreactors size requirements. Systems one tenth the size of known fed-batch processing systems can provide protein productivity equivalent or better extracellular proteins as well as overall concentration of material.

In accordance with yet another aspect of the invention, there is provided a disposable perfusion tangential flow filtering system which facilitates implementing or changing a pre-assembled, pre-sterilized perfusion tangential flow processing system without impacting the bioreactor sterility both during the operation or upon start up. The disposable perfusion tangential flow filtering system completely eliminates the need for autoclaving components. The disposable perfusion tangential flow filtering system is designed to connect to disposable, glass, and stainless steel bio reactors. The disposable perfusion tangential flow filtering system includes the disposable pumphead, hollow fiber filter and associated connections which is designed to be gentle on cells or other biological material without impacting viability and is scalable.

In accordance with still another aspect of the invention, there is provided a hollow fiber perfusion tangential flow filter system providing quick assembly to a bioreactor processing flow path Module (hollow fiber), Bag and Tubing (MBT) assembly. The MBT assembly may include a bag containing media feeding the reactor and/or a permeate bag collecting metabolic wastes. In some instances the bioreactor vessel may be a bag. The pre-sterilized processing MBT assembly includes low shear a re-circulation pumphead, automatic control of filtration sequences of operation including: the operation of seed reactors; continuous tangential flow; concentrated cell tangential flow; concentrated fed-batch tangential flow; as well as cell clarification (post transfection or cell lysis).

In accordance with another aspect of the invention, there is provided a disposable MBT assembly allowing a simple procedure for changing of the filtering loop without impacting sterility. The disposable MBT assembly eliminates the need for autoclaving components and is designed to connect to either disposable reactors, re-usable glass and stainless steel reactors. The MBT assembly is pre-sterilized providing an easily changed tangential flow processing loop without impacting sterility, is designed to connect to either disposable reactors, glass, and stainless steel reactors, without impacting viability.

In accordance with another aspect of the invention, there is provided a method for proliferation of cells within a bioreactor using tangential flow perfusion filtering. The method includes, providing a bioreactor vessel containing bioreactor fluid, providing a pre-sterilized, disposable, assembled bioreactor fluid filtering system, aseptically connecting the bioreactor vessel to the filtering system, engaging a pumphead of the filtering system with a reusable pump motor element of a control system, priming the pumphead, circulating bioreactor fluid from the bioreactor vessel through the filter system, separating the bioreactor fluid into a flow of filtered bioreactor fluid and a flow of waste fluid, returning the filtered bioreactor fluid to the bioreactor vessel, carrying the waste fluid from the filter system for disposal, disconnecting the filtering system from the bioreactor vessel, and disposing of the filtering system.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 1 is a bioreactor system according to the present invention.

FIG. 2A is a disposable portion of a tangential flow perfusion filtering system according to the present invention.

FIG. 2B is a reusable control system according to the present invention.

Corresponding reference characters indicate corresponding components throughout the several views of the drawings.

DETAILED DESCRIPTION OF THE INVENTION

Figure 3A:
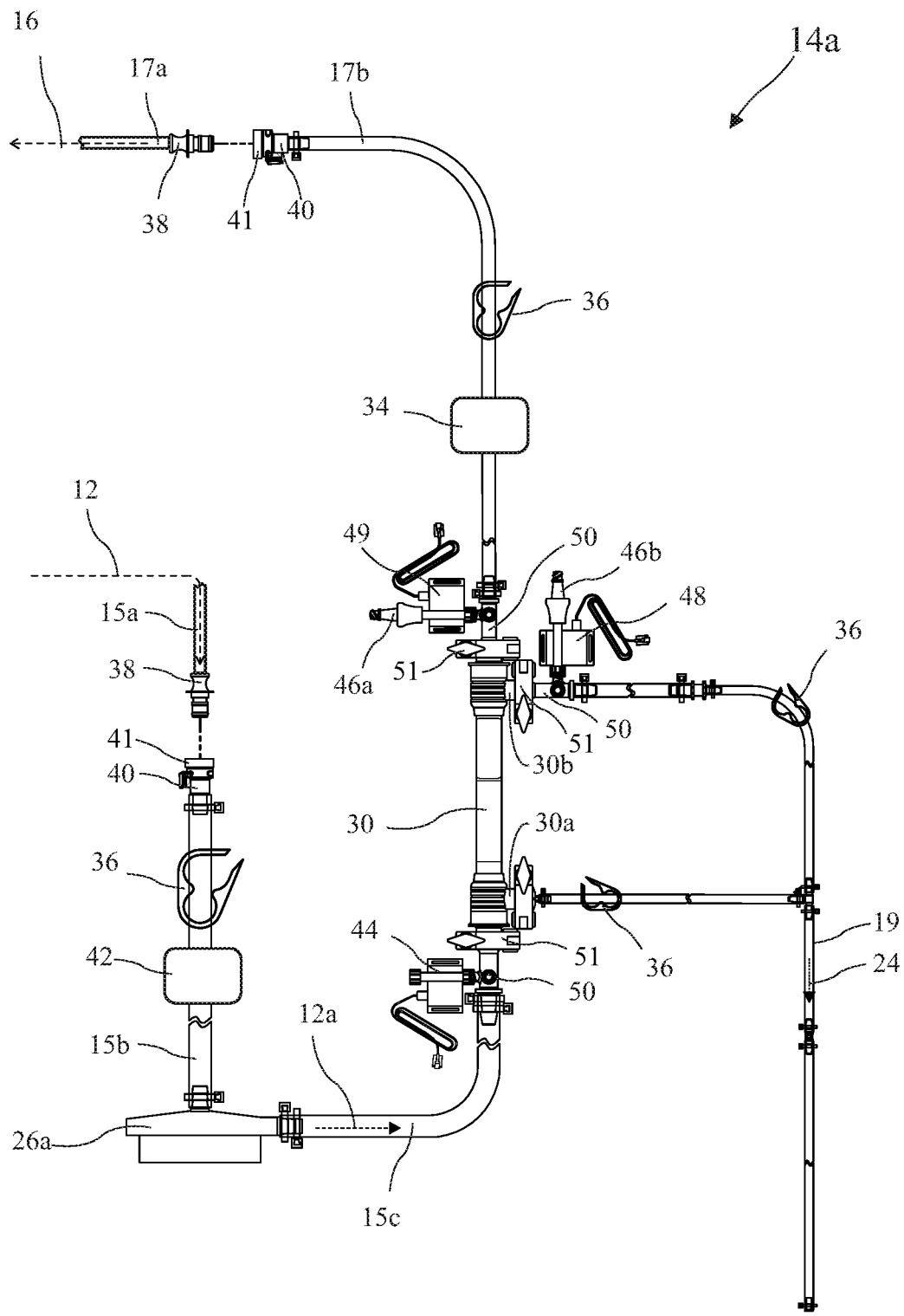
FIG. 3A shows a detailed view of a first tangential flow perfusion filtering system according to the present invention.

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Where the term "generally" is associated with an element of the invention, it is intended to describe a feature's appearance to the human perception, and not a precise measurement.

A bioreactor system 10 according to the present invention is shown in FIG. 1. The bioreactor system 10 includes a bioreactor vessel 11 containing bioreactor fluid 13, a pre-assembled and pre-sterilized, disposable, tangential flow perfusion filtering system 14, and a reusable control system 20. The filtering system 14 is connected between a bioreactor outlet 11a and bioreactor inlet 11b to receive a bioreactor material flow (or a first flow of the bioreactor fluid) 12 (see FIG. 3A) through bioreactor tubing 15 from the bioreactor 11 and return a filtered flow (or a return flow of the bioreactor fluid) 16 (see FIG. 3A-3C) through return tubing 17 to the bioreactor 11. The bioreactor system 10 cycles bioreactor fluid through the filtering system 14 which separates out metabolic wastes and/or protein waste material and thereby allows the reaction in the bioreactor vessel 11 to continue to completion allowing higher cell densities within the same bioreactor which provides greater proteins to be expressed due to this increased density of viable cells.

The bioreactor tubing 15 is preferably connected to the lowest point/dip tube on the bioreactor 11 below the sparger ring and the return tubing 17 is preferably connected to the bioreactor in the upper ¼ of the bioreactor volume and submerged in the bioreactor fluid 13.

The bioreactor vessel 11 receives the return flow of the bioreactor fluid 16 through a pre-sterilized assembly comprising a pump 26, hollow fiber filter 30, and associated fittings and connections. The pump 26 preferably includes a low shear, gamma stable, disposable, levitating pumphead 26a, for example, a model number MPD-200 low shear re-circulation pump manufactured by Levitronix in Waltham, Mass. The MPD-200 includes a magnetically levitated rotor inside a disposable pumphead, and stator windings in the pump body, allowing simple removal and replacement of the pumphead.

The flow of bioreactor material 12 passes from the bioreactor vessel 11 to the filtering system 14 and the return flow of the bioreactor fluid 16 passes from the filtering system 14 back to the bioreactor vessel 11. A permeate flow 24 (for example, a metabolic waste material flow) (see FIG.) is stripped from the flow of bioreactor material 12 by the hollow fiber perfusion filtering system 14 and away carried by waste material tubing 19. The metabolic waste, as well as associated proteins, are drawing from the hollow fiber perfusion tangential flow system 14 by a permeate pump 22 into a waste container 23.

The filtering system 14 is shown in FIG. 2A. The filtering system 14 includes a disposable pumphead 26a, which simplifies initial set up and maintenance. The pumphead 26a circulates the bioreactor fluid 12a through the hollow fiber tangential flow filter 30 and back to the bioreactor vessel 11. A non-invasive transmembrane pressure control valve 34 in line with the flow 16 from the hollow fiber tangential flow filter 30 to the bioreactor vessel 11, controls the pressure within the hollow fiber tangential flow filter 30. The permeate flow 24 is continually removed from the bioreactor fluid 13 which flows through the tangential flow hollow fiber filter 30. The pumphead 26a and the permeate pump 22 are controlled by the control system 20 to maintain the desired flow through the hollow fiber tangential flow filter 30.

A detailed view of a first pre-sterilized, pre-assembled, disposable, tangential flow perfusion filtering system 14a is shown in FIG. 3A. The filtering system 14a receives the bioreactor material flow 12 through a male sanitary connector 38 on first bioreactor fluid flow tubing 15a connected to the bioreactor 11. The connector 38 is connected to a female connector 40 on second bioreactor fluid flow tubing 15b after removing a cap 41, and the tubing 15b is connected to the pumphead 26a. The flow 12 passes through a non-invasive ultrasonic flow meter 42 and then through the disposable pumphead 26a to provide a controlled bioreactor material flow 12a through third bioreactor tubing 15c to the hollow fiber tangential flow filter 30. The tubing 15c is connected to the hollow fiber tangential flow filter 30 through a sanitary connection 50. Another sanitary connector 50 connects return tubing 17b to the hollow fiber tangential flow filter 30. A second female connector 40 on the end of the tubing 17b connects to a second male connector 38 on the end of the tubing 17a. The non-invasive TMP pressure control valve 34 located on the tubing 17b back to the bioreactor 11 can be used to maintain the correct pressure within the hollow fiber tangential flow filter 30. The flow 16 passes through aseptic connectors 38, 40 and returns to the bioreactor vessel 11.

Feed and retentate pressure sensors 44 and 49 reside in communication with the flows 12*a* and 16 respectively before and after the hollow fiber tangential flow filter 30. A connector (or retentate port) 46*a* provides access to the return flow of the bioreactor fluid 16 and specifically provides a port for priming the pumphead 26*a*. The connector 46*a* is preferably a self-closing needle free, sterile connector, for example, a CLAVE® needle free connector. The fittings 50 include nipples for attachment of the pressure sensors 44 and 49. Clamps 51 attach the fittings 50 to the filter 30. The clamps 51 are preferably a sanitary two piece clamp compressing a gasket over the connection, commonly called a TC clamp. The hollow fiber tangential flow filter 30 includes one or two ports 30*a* and 30*b* (also see FIG. 4A) in fluid communication with the permeate flow 24, for example, for the release of waste material, expressed proteins, or viruses of interest separated from the flow 12*a*. Pressure sensor 48 resides in communication with the metabolic waste material flow 24. Pinch clamps 36 reside over tubing 15*b*, 17*b*, and 19. A second connector 46*b* allows access to the permeate flow 24.

The hollow fiber tangential flow filter 30 is preferably a hollow fiber filter which may be either a microporous or ultrafilter pore size. Further, pore size can be selected depending on the operation to be performed. The pore size can be selected concentrate up expressed product in the bioreactor while passing metabolic waste, or the membrane pore size may be selected to pass products of interest the cells are expressing (for example, express proteins or viruses of interest) as well as metabolic waste. The hollow fiber tangential flow filter 30 is pre-sterilized with the associated sensors and connections, and manufactured with no biocides, and only animal free glycerine is present within the pores of the hollow fiber tangential flow filter 30. The hollow fiber tangential flow filter 30 eliminates the need for autoclaving prior to using. Preferably, a very low protein binding chemistry is used, however, polysulfone (PS) as well as other chemistries can be utilized. Preferably, a very low protein binding chemistry Modified Polyether Sulfone (mPES) membrane is used. The perfusion hollow fiber can be either a 0.5 mm lumen or 1.0 mm lumen with scaleable hollow fiber elements to accommodate varying bioreactor sizes. An example of an acceptable hollow fiber tangential flow filter 30 is a hollow fiber filter such as the KrosFlo Filter Module manufactured by Spectrum Labs in Rancho Dominguez, Calif.

The valve 34 is preferably a non-invasive valve which resides outside tubing carrying the return flow 16. The valve "squeezes" the tubing to restrict and control the flow. Such a valve 34 is non-invasive and provides a commercial advantage since the return line to the reactor is situated thru the valve to regulate the applied pressure on the membrane.

The pumphead 26*a* and hollow fiber tangential flow filter 30 in the filtering system 14*a* are preferably connected by flexible tubing allowing easy changing of the elements. Such tubing allows aseptically replacement of the hollow fiber tangential flow filter 30 during a run in case the hollow fiber pore becomes plugged, over-loaded with material which therefore provides easy exchange to a new perfusion hollow fiber assembly.

Figure 3B:
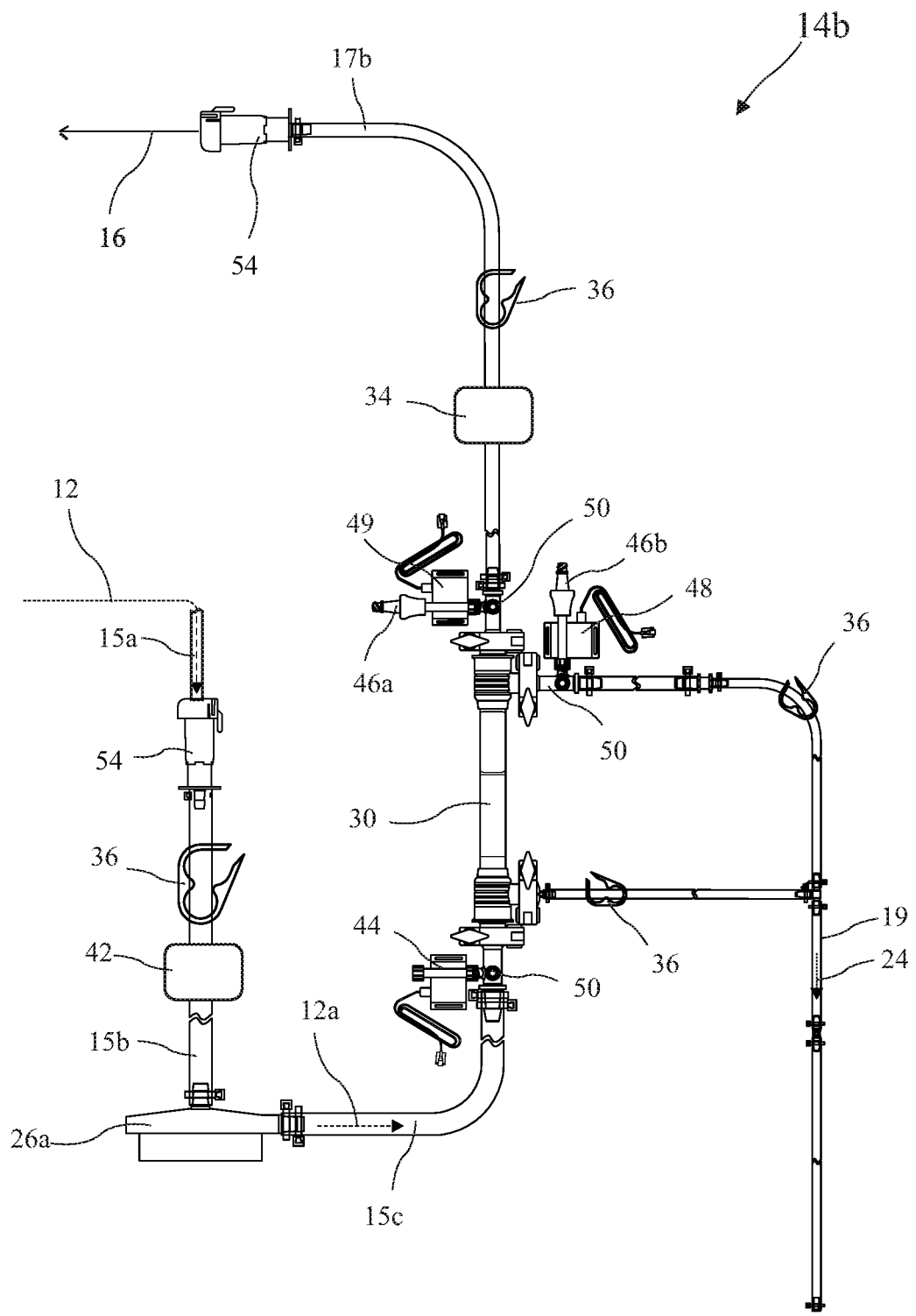
FIG. 3B shows a detailed view of a second tangential flow perfusion filtering system according to the present invention.

A second pre-sterilized, pre-assembled, tangential flow perfusion filtering system 14*b* is shown in FIG. 3B. The filtering system 14*b* replaces the connectors 38 and 40 with a first disposable aseptic connector 54. Filter systems according to the present invention may further include tube welding or aseptic connectors manufactured by GE, Pall, Millipores and other, and filtering systems according to the present invention including any aseptic connectors is intended to come within the scope of the present invention. The filtering system 14*b* is otherwise similar to the filtering system 14*a*.

Figure 3C:
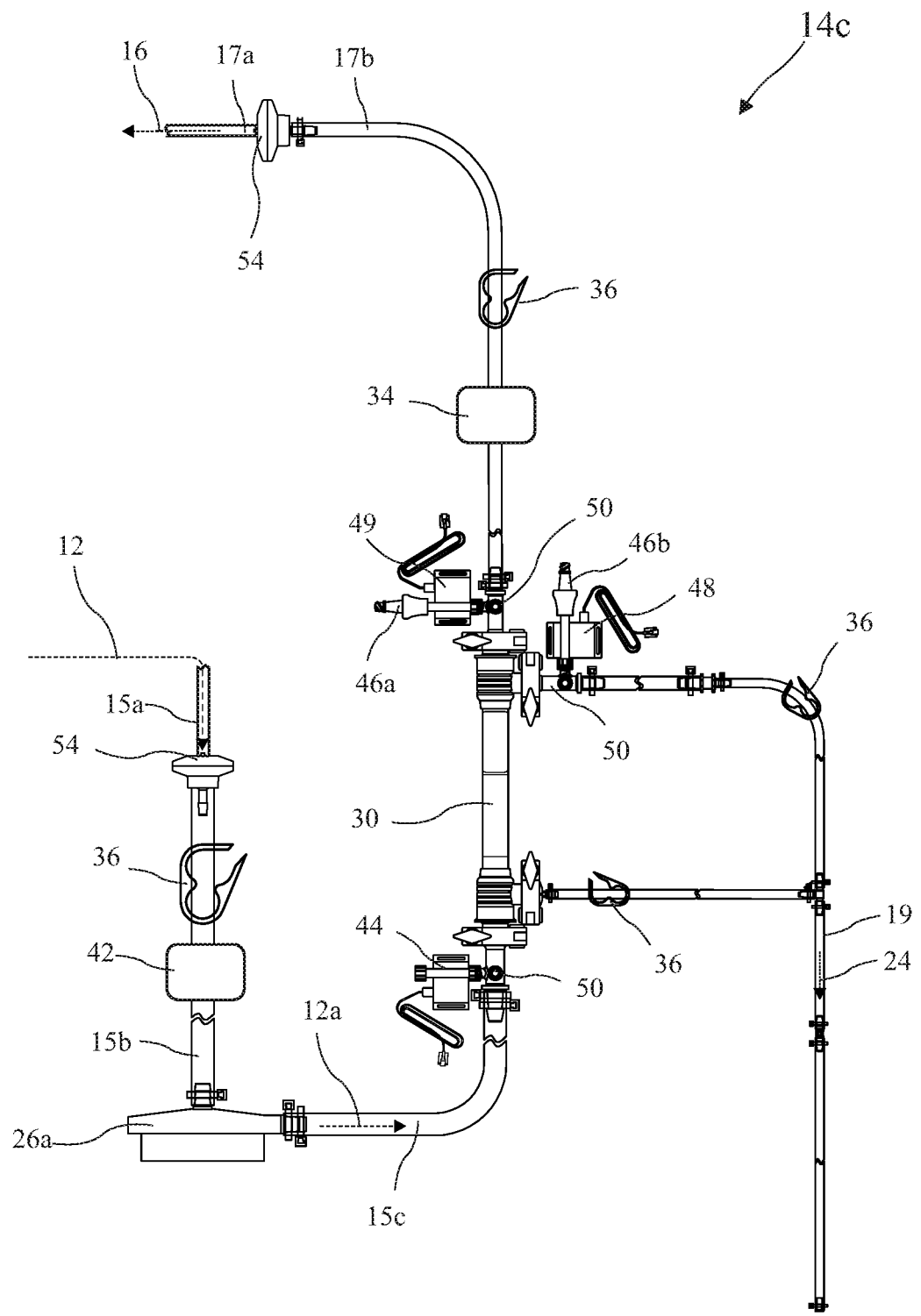
FIG. 3C shows a detailed view of a third tangential flow perfusion filtering system according to the present invention.

A third pre-sterilized and pre-assembled tangential flow perfusion filtering system 14*c* is shown in FIG. 3C. The filtering system 14*c* replaces the connectors 38 and 40 with a second disposable aseptic connector 56. The filtering system 14*c* is otherwise similar to the filtering system 14*a*.

Figure 3D:
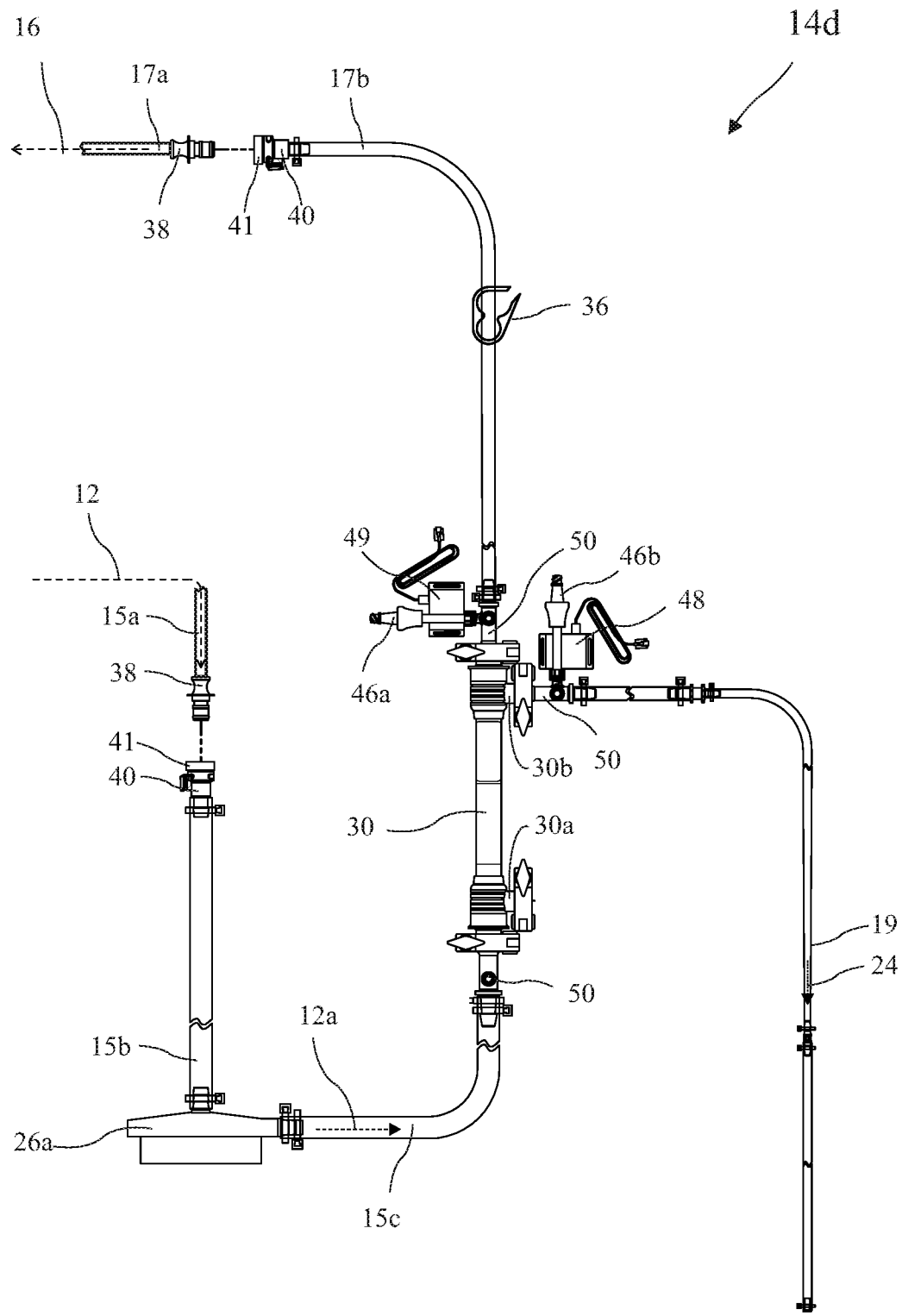
FIG. 3D shows a detailed view of a third tangential flow perfusion filtering system according to the present invention.

A fourth tangential flow perfusion filtering system 14*d* is shown in FIG. 3D. The filtering system 14*d* is simplified to remove elements not necessary for all applications and is otherwise similar to the filtering system 14*a*.

Figure 3E:
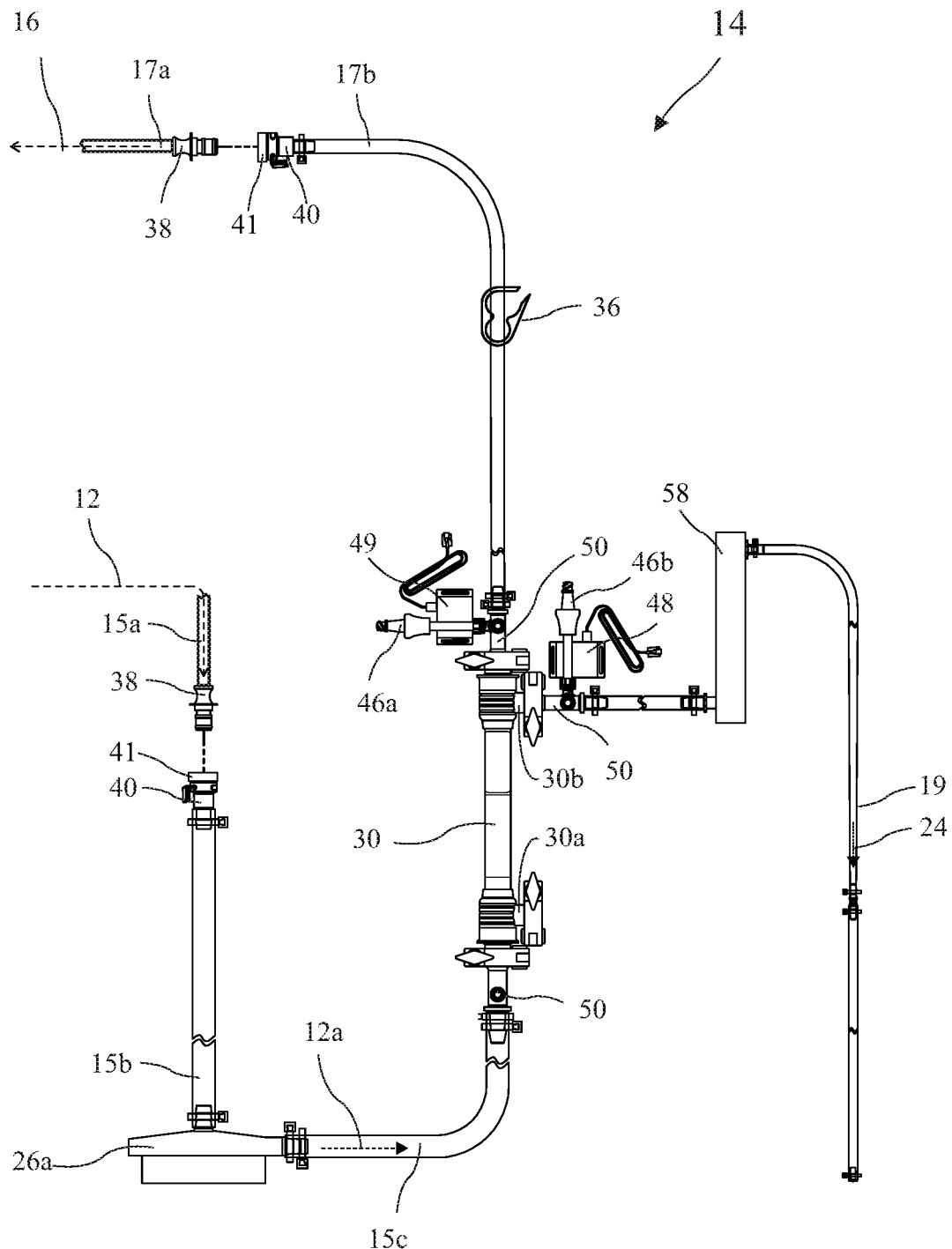
FIG. 3E shows a detailed view of a third tangential flow perfusion filtering system according to the present invention.

A fifth tangential flow perfusion filtering system 14*e* is shown in FIG. 3E. The filtering system 14*e* is also a simplified to remove elements not necessary for all applications and is otherwise similar to the filtering system 14*a*, but includes a flow meter 58 for monitoring the permeate flow 24. In some methods of use, it is desirable or necessary to match the permeate flow 24 to the bioreactor 11 in use. In other instances, the permeate is collected and weighed to monitor the system.

Figure 4A:
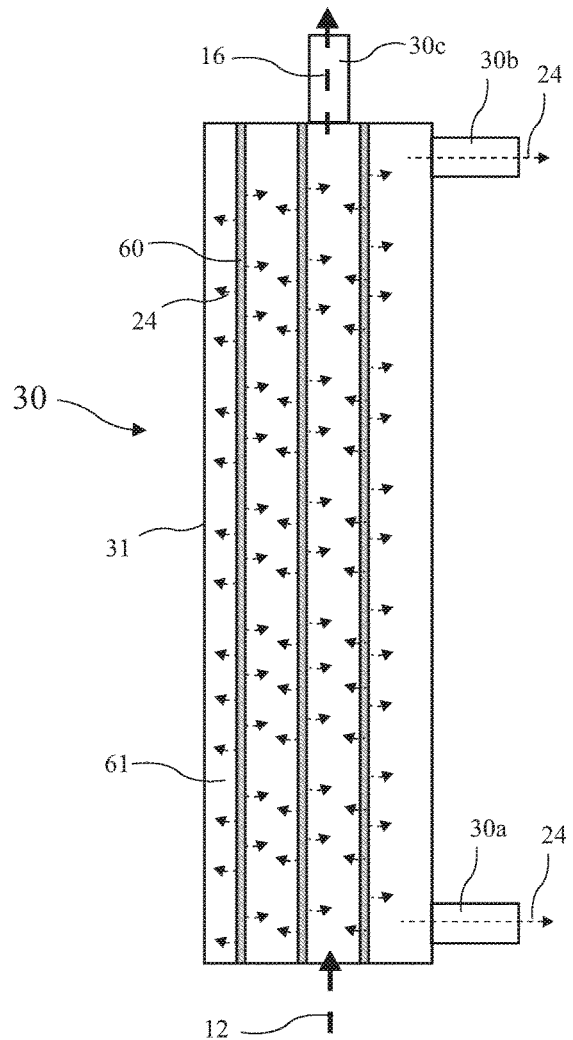
FIG. 4A shows a cross-sectional view of a hollow fiber tangential flow filter according to the present invention.

A cross-sectional view of the hollow fiber tangential flow filter 30 is shown in FIG. 4A. The hollow fiber tangential flow filter 30 includes hollow fibers 60 releasing the waste material (i.e., permeate) flow 24 into a permeate section 61 of the filter housing 31. The waste material flow 24 travels to the ports 30*a* and 30*b* and is drawn from the filter housing 31 by the permeate pump 22 (see FIG. 1). The filtered return flow (or retentate) 16 is released through retentate port 30*c*.

Figure 4B:
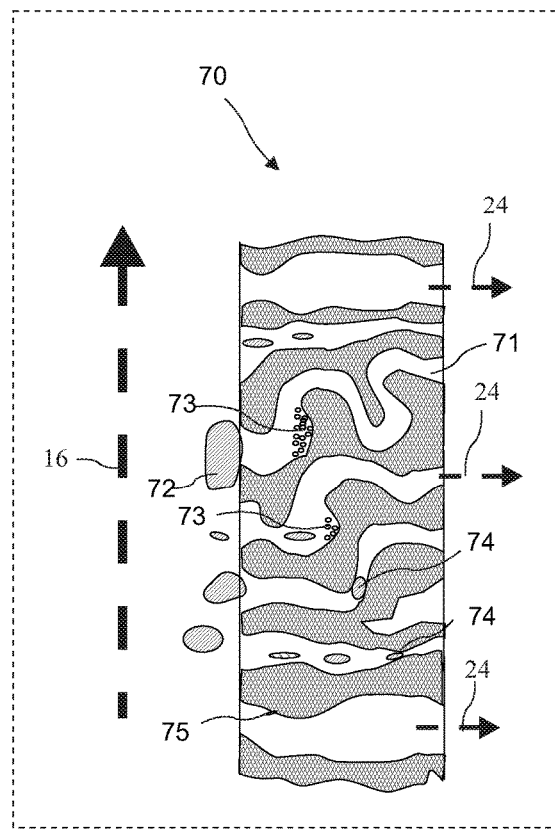
FIG. 4B shows a cross-sectional view of a wall of a thick wall hollow fiber tangential flow filter according to the present invention.

A cross-sectional view of a wall 70 of a thick wall hollow fiber tangential flow filter is shown in FIG. 4B. The wall 70 includes tortuous paths 71 to capture certain elements of the flow through the thick wall hollow fiber tangential flow filter. Surface retained material 72 too large to enter the tortuous paths 71 is retained on an interior surface of the wall 70. Setting zones 73 capture small particles which enter the tortuous paths 71. Depth strained particles 74 enter the tortuous paths 71 but become lodged in narrowing channels. Some small particles 75 become lodged in walls of the tortuous paths 71.

The settling zones 73 as well as the narrowing channels cause a separation unlike filtering obtained by the skin or surface of common thin wall tangential flow filter membranes. The thick wall hollow fiber tangential flow filter is preferably made from Polyethylene (PE) which has a molecular structure of repeating —CH2-CH2 units where the wall thickness of the fiber is in the range between 1.2 mm to 1.7 mm, providing the depth filtration of the material passing thru the wall 70.

Figure 5:
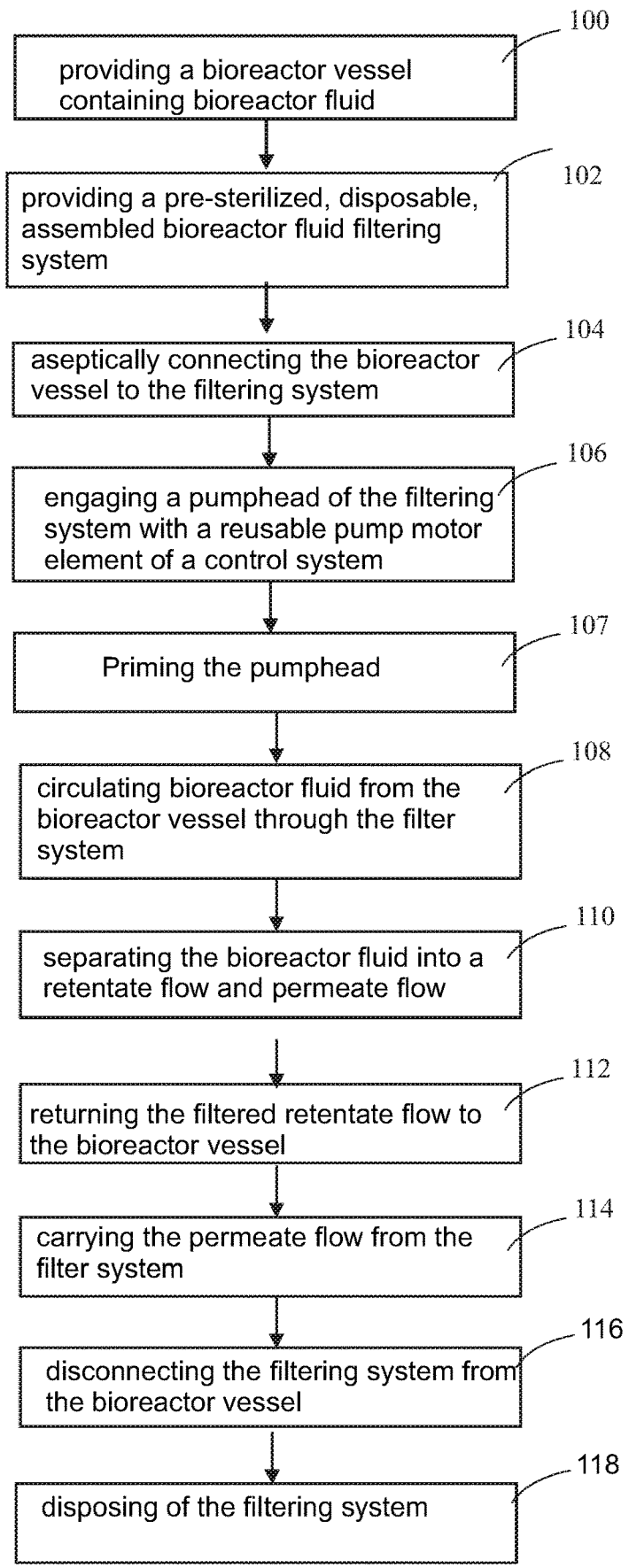
FIG. 5 shows a method according to the present invention.

A method for proliferation of cells within a bioreactor using tangential flow perfusion filtering is described in FIG. 5. The method includes, providing a bioreactor vessel containing bioreactor fluid at step 100, providing a pre-sterilized, disposable, assembled bioreactor fluid filtering system at step 102, aseptically connecting the bioreactor vessel to the filtering system at step 104, engaging a pumphead of the filtering system with a reusable pump motor element of a control system at step 106, priming the pumphead at step 107, circulating bioreactor fluid from the bioreactor vessel through the filter system at step 108, separating the bioreactor fluid into a flow of filtered bioreactor fluid and a flow of waste fluid at step 110, returning the filtered bioreactor fluid to the bioreactor vessel at step 112, carrying the waste fluid from the filter system for disposal at step 114, disconnecting the filtering system from the bioreactor vessel at step 116, and disposing of the filtering system at step 118.

The pinch clamps 36 are used to block the tubing 15b, 17b, and 19 during priming of the flow path as well as utilized during the shutdown of the flow path for discarding the filter system 14.

The feed and retentate pressure sensors 44 and 49 respectively monitor operating conditions based upon the flow and changes in viscosity/cell density as the process ages. The feed and retentate pressure sensors 44 and 49 are used during operation to monitor these changes in the cell conditions within the reactor at a give recirculation flow rate (fiber shear rate). The permeate pressure sensor 49 is used to ensure the permeate pump 22 is not running to fast. A high permeate pump speed results in pulling a vacuum on the hollow fibers 60 which may inadvertently foul the pores on the hollow fibers 60. Process loop controls are put in place to ensure correct operation of the hollow fiber tangential flow filter 30 as well as pressure associate alarms/system shut down to ensure safe perfusion operations.

While the invention herein disclosed has been described by means of specific embodiments and applications thereof, numerous modifications and variations could be made thereto by those skilled in the art without departing from the scope of the invention set forth in the claims.

I claim:

1. A method of assembling a system for tangential flow perfusion filtering, the system comprising
   (a) a bioreactor vessel containing bioreactor fluid, the bioreactor fluid comprising cells residing in the bioreactor vessel, the cells including cells produced in the bioreactor vessel and additional material residing in the bioreactor vessel including at least one of waste material, expressed proteins, and viruses of interest,
   (b) a first bioreactor fluid flow tubing in fluid communication with the bioreactor vessel,
   (c) bioreactor return tubing in fluid communication with the bioreactor vessel,
   (d) a disposable pumphead and tangential flow filter unit wherein the pumphead and tangential flow filter unit are assembled and pre-sterilized, configured for attachment to the bioreactor vessel and comprising in serial order of flow:
   a first aseptic connector sealed by a first cap;
   a second bioreactor fluid flow tubing connected to the first aseptic connector;
   the disposable pumphead connected to the second bioreactor fluid flow tubing;
   a third bioreactor fluid flow tubing connected to the disposable pumphead;
   the tangential flow filter unit connected to the third bioreactor fluid flow tubing;
   permeate tubing connected to a permeate port of the tangential flow filter unit;
   a retentate return tubing connected to a retentate port of the tangential flow filter unit; and
   a second disposable aseptic connector connected to the retentate return tubing and sealed by a second cap, and
   (e) a reusable control system including a reusable pump motor configured for cooperation with the disposable pumphead;
   the method of assembling the system consisting of:
   attaching the assembled, pre-sterilized pumphead and tangential flow filter unit to the bioreactor vessel, wherein the assembled, pre-sterilized pumphead and tangential flow filter unit includes said first aseptic connector and said second aseptic connector, by:
   removing the first cap from the first aseptic connector;
   aseptically connecting the first bioreactor fluid flow tubing to the first aseptic connector;
   removing the second cap from the second aseptic connector;
   aseptically connecting the bioreactor return tubing to the second aseptic connector;
   engaging the disposable pumphead with the reusable pump motor;
   the disposable pumphead circulating the bioreactor fluid through the tangential flow filter; thereby separating the bioreactor fluid into a retentate flow comprising the cells that is returned from the tangential flow filter unit through the retentate return tubing to the bioreactor vessel and a permeate flow comprising the additional material that is removed from the tangential flow filter unit through the permeate tubing; and
   optionally, connecting a permeate pump to the permeate tubing to draw the permeate flow from the tangential flow filter unit.

2. The method of claim 1, wherein the tangential flow filter unit includes pore membranes greater than 0.1 micron which remove the additional material.

3. The method of claim 2, wherein tangential flow filter unit is a Modified Polyether Sulfone (mPES) membrane hollow fiber tangential flow filter.

4. The method of claim 1, wherein the disposable pumphead is a low shear disposable pumphead.

5. The method of claim 4, wherein the disposable pumphead is a low shear, gamma stable, disposable pumphead.

6. The method of claim 5, wherein the disposable pumphead is a levitating pumphead.

7. The method of claim 1, wherein the second fluid flow tubing, third fluid flow tubing and retentate return tubing are flexible tubings allowing easy assembly of the system.

\* \* \* \* \*